United States Patent [19]

Nofre et al.

[11] Patent Number: 4,935,517
[45] Date of Patent: Jun. 19, 1990

[54] SWEETENING AGENTS DERIVED FROM N-HYDROCARBON-SUBSTITUTED L-ASPARTIC AND L-GLUTAMIC ACIDS

[75] Inventors: Claude Nofre, Lyon; Jean M. Tinti, Meyzieu, both of France

[73] Assignee: Universite Claude Bernard, France

[21] Appl. No.: 341,703

[22] Filed: Apr. 21, 1989

[30] Foreign Application Priority Data

Apr. 22, 1988 [FR] France .................. 88 05644

[51] Int. Cl.$^5$ ............. C07D 239/42; C07D 213/75; C07C 121/52
[52] U.S. Cl. .................... 544/322; 546/289; 558/412; 558/414
[58] Field of Search ............. 558/412, 414; 546/289; 544/322

[56] References Cited

U.S. PATENT DOCUMENTS 4,673,582  6/1987  Nofre et al. .................. 558/414

OTHER PUBLICATIONS

Chemical Abstracts, vol. 107 (1987), Abst. No. 196,772 to Tsuchiya et al.
Chemical Abstracts, vol. 109 (1988), Abst. No. 93,603 to Tsuchiya et al.

Primary Examiner—Joseph Paul Brust
Assistant Examiner—Mary Sue Howard
Attorney, Agent, or Firm—Lerner, David, Littenberg, Krumholz & Mentlik

[57] ABSTRACT

Sweetening agents of the general formula:

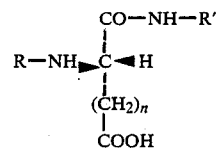

wherein R is a saturated or unsaturated, acyclic, cyclic or mixed hydrocarbon group having 5 to 13 carbon atoms, wherein R' is, in a preferred embodiment, a 4-cyanophenyl or 2-cyanopyrid-5-yl group, and wherein n is equal to 1 or 2.

3 Claims, No Drawings

SWEETENING AGENTS DERIVED FROM N-HYDROCARBON-SUBSTITUTED L-ASPARTIC AND L-GLUTAMIC ACIDS

BACKGROUND

The present invention relates to new sweetening agents, which are useful in particular for sweetening foods, beverages, confectioneries, pastries, chewing gums, hygiene products, cosmetics, toiletries, pharmaceutical and veterinary products and their equivalents.

U.S. Pat. Nos. 3,725,453 and 3,775,460 have described sweetening agents derived from L-aspartic acid and having the following general formula:

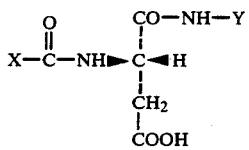

wherein X is $CF_3$ or $CCl_3$ and wherein Y is 4—C-N—$C_6H_4$, 4—Cl-6$H_4$, 4—Br—$C_6H_4$, 4F—$C_6H_4$ or $C_6H_5$.

Tinti et al. have shown that the L-aspartyl residue of the preceding compounds can be replaced, often advantageously, by its higher homolog, the L-glutamyl residue (Naturwissenschaften, 1981, 68, 143).

Tsuchiya et al. have described as sweetening agents, compounds of the formula:

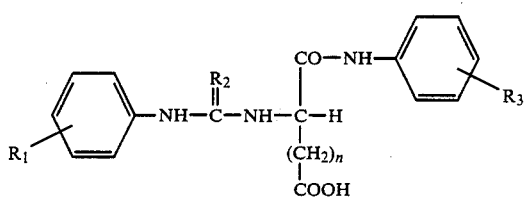

ps wherein $R_1$ and $R_3$ are H, the halogens, CN, $NO_2$, R' (R' being a $C_1$–$C_6$ alkyl group), COOR'' (R'' being a $C_1$–$C_4$ alkyl group), R''CO, halomethyl, R''O, CONHR'', $SO_2R''$ or SOR'', wherein $R_2$ is O or S, and wherein n is 0, 1 or 2 (Japanese Patent No. 86-260052), or of the formula:

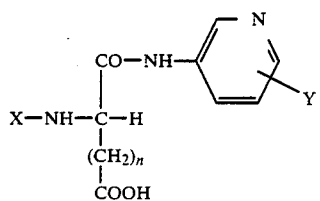

wherein X is $CF_3CO$ or $CCl_3CO$, wherein Y is CN or $NO_2$ and wherein n is 1 or 2 (Japanese Patent No. 87-132863), or of the formula:

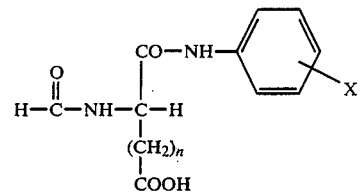

wherein X is CN or $NO_2$ and wherein n is 1 or 2 (Japanese Patent No. 87-132847), or of the formula:

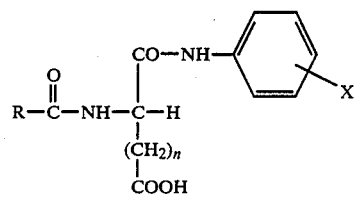

wherein X is CN or $NO_2$, wherein R is H, a $C_1$–$C_{10}$ alkyl group or an alkoxy or aryloxy aromatic group and wherein n is 1 or 2 (Japanese Patent No. 87-252754).

The compounds described in the prior art are therefore all N-formyl, N-acyl, N-carbamoyl or N-thiocarbamoyl carbamoyl derivatives of aspartic or glutamic acid alphamonamides. They therefore have a carbonyl group C=O or a thiocarbonyl group C=S fixed directly to the alpha-amino group of the aspartyl or glutamyl residue.

The major disadvantage of these N-formyl, N-acyl, N-carbamoyl or N-thiocarbamoyl derivatives for their use as sweetening agents lies in their poor stability in aqueous solution, and thus under the conditions of use that are normal for synthetic sweetening agents, because of the ease of hydrolysis of their N-formyl, N-acyl, N-carbamoyl or N-thiocarbamoyl part, with corresponding reduction of the sweetening power, which circumstance considerably limits their possible industrial application.

BRIEF SUMMARY OF THE INVENTION, AND DETAILED DESCRIPTION

The sweetening agents of the present invention have the following general formula:

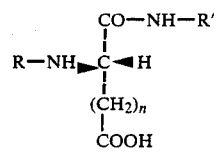

wherein:
R is a saturated or unsaturated, acyclic, cyclic or mixed hydrocarbon group having 5 to 13 carbon atoms;
R' is a 4-cyanophenyl, 2-cyanopyrid-5-yl or 2-cyanopyrimidin-5-yl group; and
n is 1 or 2.
Advantageously:
R is selected from the group consisting of:
normal alk(en)yl $C_5$–$C_{13}$,
branched alk(en)yl $C_5$–$C_{13}$,
cycloalk(en)yl alk(en)yl $C_5$–$C_{13}$, alkyl cycloalk(en)yl alk(en)yl $C_6$–$C_{13}$,
bicycloalk(en)yl alk(en)yl $C_8$–$C_{13}$,
fused bicycloalk(en)yl alk(en)yl alk(en)yl $C_8$–$C_{13}$.

In a preferred embodiment, R is selected from the group consisting of:
$CH_3(CH_2)_4$,
$CH_3(CH_2)_5$,
$CH_3(CH_2)_6$,
$CH_3(CH_2)_7$,
$CH_3(CH_2)_2CH\!=\!CHCH_2$,
$CH_3CH\!=\!CHCH\!=\!CHCH_2$,
$CH_3(CH_2)_2CH(CH_3)CH_2$,
$CH_3(CH_2)_3CH(CH_3)CH_2$,
$CH_3(CH_2)_4CH(CH_3)CH_2$,
$(CH_3)_2CH(CH_2)_4$,
$(CH_3)_2CH(CH_2)_5$,
c—$C_6H_{11}CH_2$,
c—$C_6H_{11}CH(CH_3)CH_2$,
c—$C_6H_{11}(CH_2)_3$,
c—$C_6C_{11}CH_2CH(CH_3)CH_2$,
$C_6H_5CH_2$,
$C_6H_5(CH_2)_2$,
$C_6H_5(CH_2)_3$,
$C_6H_5CH(CH_3)CH_2$,
$C_6H_5CH_2CH(CH_3)CH_2$,
$[(CH_3)_3C]_2CH(CH_2)_3$,
$[(CH_3)_3C_2CHCH_2CH(CH_3)CH_2$,
(c—$C_3H_5)_2CH(CH_2)_3$,
(c—$C_3H_5)_2CHCH_2CH(CH_3)CH_2$,
$C_6H_5CH\!=\!CHCH_2$,
c—$C_6H_{11}CH\!=\!CHCH_2$,
1-naphthylpropyl,
1-perhydronaphthylpropyl
1-indenylpropyl,
1-indanylpropyl,
1-perhydroindenylpropyl,
2,2,5,5-tetramethylcyclopentylpropyl,
2-methyl-3-indenylpropyl,
2-methyl-3-indanylpropyl, or
2-methyl-3-(2,2,5,5-tetramethylcyclopentyl)propyl.

In other words, the sweetening agents of the present invention are distinguished from the proposed compounds of the prior art cited in the introduction in that they are N-hydrocarbon-substituted derivatives of L-aspartic or L-glutamic acid in the form of N-aryl or N-heteroaryl alpha-amides. At the chemical level, therefore, they are distinguished fundamentally from the N-formyl, N-acyl, N-carbamoyl or N-thiocarbamoyl derivatives described in the prior art.

Moreover, in contrast to certain of the compounds cited in the prior art, the N-hydrocarbon-substituted derivatives of aspartic and glutamic acid of the invention have a sweetening activity only in their L configuration, as is apparent from the general formula, in which the bonds to the asymmetric carbon are represented by a triangle for the bonds above the plane and by a broken line for the bonds below the plane.

The compounds of the invention constitute the first known derivatives of N-hydrocarbon-substituted alpha-amino acids having sweetening character. The production of a sweetening activity in these N-hydrocarbon-substituted derivatives is all the more unexpected in view of the knowledge that any modification, even slight, of the molecular structure of a sweetening agent can cause suppression of the sweetening activity, especially since the relationships between the structure and the sweetening activity are unpredictable. See, for example, M. G. J. BEETS, Structure-Activity Relationships in Human Chemoreception, Applied Science Pub., London, 1978, pp. 259–362; H. VAN DER WEL, A. VAN DER HEIJDEN, H. G. PEER, Food Reviews International, 1987, , 193–268.

In addition, this replacement of the N-formyl, N-acyl, N-carbamoyl or N-thiocarbamoyl groups by a N-hydro-carbon-substituted group has the effect of strongly enhancing the sweetening activity, since it is possible to obtain, with certain of the compounds of the present invention, a sweetening activity which is as much as 7000 times greater than that of sucrose, i.e., at least 2 to 3 times greater than that of the most potent N-acyl compounds described in the prior art cited above. This spectacular increase in the sweetening activity has the double advantage of not only lowering the costs of utilization of these compounds but also reducing the toxicological risks by decreasing the quantities necessary to sweeten the food preparations.

The replacement of the N-formyl, N-acyl, N-carbamoyl or N-thiocarbamoyl groups by an N-hydrocarbon-substituted group also unexpectedly improves the stability in solution of these compounds, so that it should be possible to use them successfully in the preparation of beverages or foods, in contrast to the N-formyl, N-acyl, N-carbamoyl or N-thiocarbamoyl derivatives. In fact, under the conditions of utilization at acid pH, which is generally the case of carbonated beverages which represent the most important share of the market for sweetening agents, the compounds of the prior art cited above herein have poorer stability than that of the compounds of the present invention. For example, it has been possible to observe, by accelerated aging, i.e., prolonged heating of a solution of pH 3 at a temperature of 70° C., that the (S)-3-(4-cyanophenylcarbamoyl)-3-(phenylmethylamino)propanoic acid described in the examples is approximately 3 times more stable than the N-trifluoroacetyl-alpha-L-aspartyl-4-cyanoanilide acid described in U.S. Pat. No. 3,725,453.

The compounds of the present invention can be prepared by various methods already generally described in the literature.

One of the preferred methods consists of condensing the amino precursor of the following general formula:

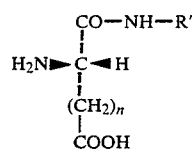

with a $C_5$–$C_{13}$ hydrocarbon-substituted aldehyde or ketone, the resulting imine being reduced by sodium cyanoborohydride by means of the technique of reductive N-monoalkylation of alpha-amino acids described by Ohfune et al., Chem. Letters, 1984, 441–444. The reaction is carried out at room temperature in methanol.

The sweetening agents of the invention can also be salified by physiologically acceptable inorganic or organic acids or bases, which has the effect of improving their solubility and/or their stability. Advantageously, these compounds are salified in the form of a hydrochloride or of sodium, potassium, ammonium, calcium or magnesium salts.

The purification of the compounds of the invention, in their acid or salified form, is realized by standard techniques such as recrystallization or chromatography.

Their structure and their purity were checked by classical techniques such as thin-layer chromatography, high-performance liquid chromatography, infrared spectrometry, nuclear magnetic resonance and elemental analysis.

The sweetening agents of the present invention can be added to any comestible product to which it is desired to impart a sweet taste, provided they are added in proportions sufficient to attain the desired level of sweetness. The optimum utilization concentration of the sweetening agent will depend on diverse factors such as the sweetening potency of the sweetening agent, the conditions of storage and utilization of the products, the particular constituents of the products, the flavor profile of the comestible products and the desired level of sweetness. Any person skilled in the art can easily determine the optimum proportion of sweetening agent which must be employed to obtain a comestible product by using routine sensory analyses. The sweetening agents of the present invention are generally added to comestible products in proportions which range, depending on the sweetening potency of the compound, from 50 mg to 500 mg of sweetening agent per kilogram or per liter of comestible product. The concentrated products obviously will contain higher percentages of sweetening agent, and will then be diluted according to the ultimate utilization purposes.

The sweetening agents of the present invention can be added in pure form to comestible products to impart a sweet taste thereto. Nevertheless, by virtue of their high sweetening potency, they are generally admixed with an appropriate carrier or bulking agent.

The sweetening potency of the compounds described in the examples was evaluated by a group of eight experienced human tasters. For this purpose, the compounds, in aqueous solution in various concentrations, are compared in terms of taste with a control solution of sucrose in a concentration of 2% by weight. The sweetening potency of the compound tested by comparison with sucrose then corresponds to the weight ratio which exists between the compound and sucrose at equal sweetening intensity, i.e., when the sweet tastes of the solutions of the tested compound and of the control solution of sucrose are considered by a majority of tasters to have the same sweetening intensity.

EXAMPLES

The manner in which the invention can be realized and the advantages which derive therefrom will be understood more clearly by the practical example which follows and which relates to the synthesis of (S)-3-(4-cyanophenylcarbamoyl)-3-(phenylmethylamino)propanoic acid, the formula of which is:

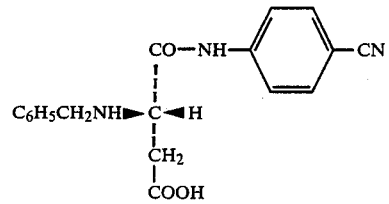

To prepare this compound, 1.59 g (0.015 mol) of benzaldehyde is added to a mixture of 2.35 g (0.01 mol) of alpha-L-aspartyl-4-cyanoanilide and 0.62 g (0.01 mol) of sodium cyanoborohydride. The solution is stirred for 3 days at 20° C. and then is filtered before being concentrated to dryness under vacuum. The residue is dissolved in a 3% sodium carbonate solution (30 cm$^3$). The solution obtained is washed with ethyl ether (3×50 cm$^3$) and then acidified to a pH of approximately 5 to 6 by 3 N HCl, yielding 0.38 g of (S)-3-(4-cyanophenylcarbamoyl)-3-(phenylmethylamino)propanoic acid (yield 12%; melting point 178° C.).

The sweetening potency of this compound corresponds approximately, on a weight basis, to 1000 (one thousand) times that of sucrose by comparison with a 2% sucrose solution.

The table below presents, by way of examples, a list of compounds of the invention obtained by an experimental procedure substantially identical to that described above. This table also contains the yields obtained, the melting points expressed in degrees Celsius (° C.) and the sweetening potency established by comparison with a 2% sucrose solution.

EXAMPLES

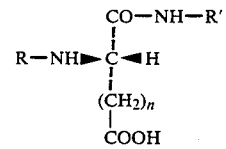

| R | R' | n | Yield (%) | m.p. (°C.) | Sweetening potency |
|---|---|---|---|---|---|
| CH$_3$(CH$_2$)$_3$CH$_2$ | 4-CN-C$_6$H$_4$ | 1 | 18 | 172 | 300 |
| CH$_3$(CH$_2$)$_4$CH$_2$ | 4-CN-C$_6$H$_4$ | 1 | 56 | 140 | 600 |
| CH$_3$(CH$_2$)$_5$CH$_2$ | 4-CN-C$_6$H$_4$ | 1 | 54 | 142 | 2,000 |
| CH$_3$(CH$_2$)$_6$CH$_2$ | 4-CN-C$_6$H$_4$ | 1 | 49 | 140 | 400 |
| (CH$_3$CH$_2$)$_2$CHCH$_2$ | 4-CN-C$_6$H$_4$ | 1 | 53 | 156 | 200 |
| (CH$_3$)$_2$CHCH$_2$CH$_2$ | 4-CN-C$_6$H$_4$ | 1 | 17 | 187 | 100 |
| c-C$_6$H$_{11}$CH$_2$ | 4-CN-C$_6$H$_4$ | 1 | 8 | 186 | 200 |
| c-C$_6$H$_{11}$CH(CH$_3$) | 4-CN-C$_6$H$_4$ | 1 | 41 | 184 | 200 |
| C$_6$H$_5$CH$_2$ | 4-CN-C$_6$H$_4$ | 1 | 12 | 178 | 1,000 |
| C$_6$H$_5$CH$_2$CH$_2$ | 4-CN-C$_6$H$_4$ | 1 | 44 | 179 | 300 |
| CH$_3$(CH$_2$)$_3$CH$_2$ | 4-CN-C$_6$H$_4$ | 2 | 25 | 134 | 1,500 |
| CH$_3$(CH$_2$)$_4$CH$_2$ | 4-CN-C$_6$H$_4$ | 2 | 36 | 142 | 5,000 |
| CH$_3$(CH$_2$)$_5$CH$_2$ | 4-CN-C$_6$H$_4$ | 2 | 74 | 143 | 7,000 |
| CH$_3$(CH$_2$)$_6$CH$_2$ | 4-CN-C$_6$H$_4$ | 2 | 76 | 135 | 2,000 |
| (CH$_3$)$_2$CHCH$_2$CH$_2$ | 4-CN-C$_6$H$_4$ | 2 | 15 | 173 | 800 |
| CH$_3$(CH$_2$)$_2$CH(CH$_3$)CH$_2$ | 4-CN-C$_6$H$_4$ | 2 | 63 | 127 | 5,000 |

-continued
EXAMPLES $$\begin{array}{c} CO-NH-R' \\ | \\ R-NH\blacktriangleright C\blacktriangleleft H \\ | \\ (CH_2)_n \\ | \\ COOH \end{array}$$

| R | R' | n | Yield (%) | m.p. (°C.) | Sweetening potency |
|---|---|---|---|---|---|
| $CH_3(CH_2)_2CH=CHCH_2$ | $4\text{-CN-}C_6H_4$ | 2 | 50 | 138 | 3,000 |
| $CH_3CH=CHCH=CHCH_2$ | $4\text{-CN-}C_6H_4$ | 2 | 36 | 140 | 2,000 |
| $C_6H_5CH_2$ | $4\text{-CN-}C_6H_4$ | 2 | 16 | 157 | 20 |
| $C_6H_5CH=CHCH_2$ | $4\text{-CN-}C_6H_4$ | 2 | 39 | 140 | 2,000 |
| $C_6H_5CH(CH_3)CH_2CH_2$ | $4\text{-CN-}C_6H_4$ | 2 | 32 | 138 | 400 |
| $c\text{-}C_6H_{11}CH_2CH_2CH_2$ | $4\text{-CN-}C_6H_4$ | 2 | 67 | 145 | 7,000 |
| $C_6H_5CH_2CH_2$ | $4\text{-CN-}C_6H_4$ | 2 | 37 | 125 | 300 |
| $C_6H_5CH_2CH_2CH_2$ | $4\text{-CN-}C_6H_4$ | 2 | 59 | 149 | 800 |
| $CH_3(CH_2)_5CH_2$ | 2-CN-5-pyrid-5-yl | 2 | 26 | 146 | 4,000 |

We claim:

1. A sweetening agent of the general formula:

$$\begin{array}{c} CO-NH-R' \\ | \\ R-NH\blacktriangleright C\blacktriangleleft H \\ | \\ (CH_2)_n \\ | \\ COOH \end{array}$$

wherein:
R is a saturated or unsaturated, acyclic, cyclic or mixed hydrocarbon group having 5 to 13 carbon atoms;
R' is a 4-cyanophenyl, 2-cyanopyrid-5-yl or 2-cyanopyrimidin-5-yl group; and
n is 1 or 2.

2. A sweetening agent according to claim 1, wherein R is selected from the group consisting of:
normal alk(en)yl $C_5$-$C_{13}$,
branched alk(en)yl $C_5$-$C_{13}$,
cycloalk(en)yl alk(en)yl $C_5$-$C_{13}$,
alkyl cycloalk(en)yl alk(en)yl $C_6$-$C_{13}$,
bicycloalk(en)yl alk(en)yl $C_8$-$C_{13}$, or
fused bicycloalk(en)yl alk(en)yl $C_8$-$C_{13}$.

3. A sweetening agent according to claim 1, wherein R is selected from the group consisting of:
$CH_3(CH_2)_4$,
$CH_3(CH_2)_5$,
$CH_3(CH_2)_6$,
$CH_3(CH_2)_7$,
$CH_3(CH_2)_2CH=CHCH_2$,
$CH_3CH=CHCH=CHCH_2$,
$CH_3(CH_2)_2CH(CH_3)CH_2$,
$CH_3(CH_2)_3CH(CH_3)CH_2$,
$CH_3(CH_2)_4CH(CH_3)CH_2$,
$(CH_3)_2CH(CH_2)_4$,
$(CH_3)_2CH(CH_2)_5$,
$c-C_6H_{11}CH(CH_3)CH_2$,
$c-C_6H_{11}CH(CH_3)CH_2$,
$c-C_6H_{11}(CH_2)_3$,
$c-C_6H_{11}CH_2CH(CH_3)CH_2$,
$C_6H_5(CH_2$,
$C_6H_5(CH_2)_2$,
$C_6H_5(CH_2)_3$,
$C_6H_5CH(CH_3)CH_2$,
$C_6H_5CH_2CH(CH_3)CH_2$,
$[(CH_3)_3C]_2CH(CH_2)_3$,
$[(CH_3)_3C]_2CHCH_2CH(CH_3)CH_2$,
$(c-C_3H_5)_2CH(CH_2)_3$,
$(c-C_3H_5)_2CHCH_2CH(CH_3)CH_2$,
$C_6H_5CH=CHCH_2$,
$c-C_6H_{11}CH=CHCH_2$,
1-naphthylpropyl,
1-perhydronaphthylpropyl,
1-indenylpropyl,
1-indanylpropyl,
1-perhydroindenylpropyl,
2,2,5,5-tetramethylcyclopentylpropyl,
2-methyl-3-indenylpropyl,
2-methyl-3-indanylpropyl, or
2-methyl-3-(2,2,5,5-tetramethylcyclopentyl)propyl.

* * * * *